United States Patent [19]

Mayer

[11] 4,018,846

[45] Apr. 19, 1977

[54] METHOD FOR CONTINUOUSLY CONTROLLING THE WATER CONTENT OF SULFURIC ACID ALKYLATION CATALYST

[75] Inventor: Ivan Mayer, Summit, N.J.

[73] Assignee: Exxon Research and Engineering Company, Linden, N.J.

[22] Filed: Dec. 29, 1975

[21] Appl. No.: 645,270

[52] U.S. Cl. .................. 260/683.59; 235/151.34
[51] Int. Cl.² ........................................ C07C 3/54
[58] Field of Search ............. 260/683.47, 683.58, 260/683.59, 683.62

[56] References Cited

UNITED STATES PATENTS

| | | | |
|---|---|---|---|
| 2,592,063 | 4/1952 | Persyn, Jr. | 260/683.59 |
| 2,765,218 | 10/1956 | Amir | 260/683.59 |
| 3,173,969 | 3/1965 | Kapff | 260/683.59 |
| 3,513,220 | 5/1970 | Brandel | 260/683.59 |
| 3,625,655 | 12/1971 | Culp et al. | 260/683.59 |
| 3,733,473 | 5/1973 | Child et al. | 260/683.59 |
| 3,864,346 | 2/1975 | Child et al. | 260/683.59 |

Primary Examiner—George Crasanakis
Attorney, Agent, or Firm—John W. Ditsler

[57] ABSTRACT

The water content of an alkylation catalyst comprising water and an acid selected from the group consisting of sulfuric acid and fluorosulfuric acid is determined continuously by contacting fuming sulfuric acid with said catalyst in a flow ratio sufficient to maintain the mixture thus formed at the point of incipient fuming. The presence of $SO_3$ evolved therefrom is determined by use of an $SO_3$ detector. The flow ratio at the point of incipient fuming is a direct measure of the amount of water in the alkylation catalyst stream. The water content thus measured is then compared to the desired water content and a signal corresponding to the deviation is used to vary the rate of fresh acid makeup to the alkylation reaction zone so as to maintain the desired water content of the catalyst in said reaction zone.

7 Claims, 1 Drawing Figure

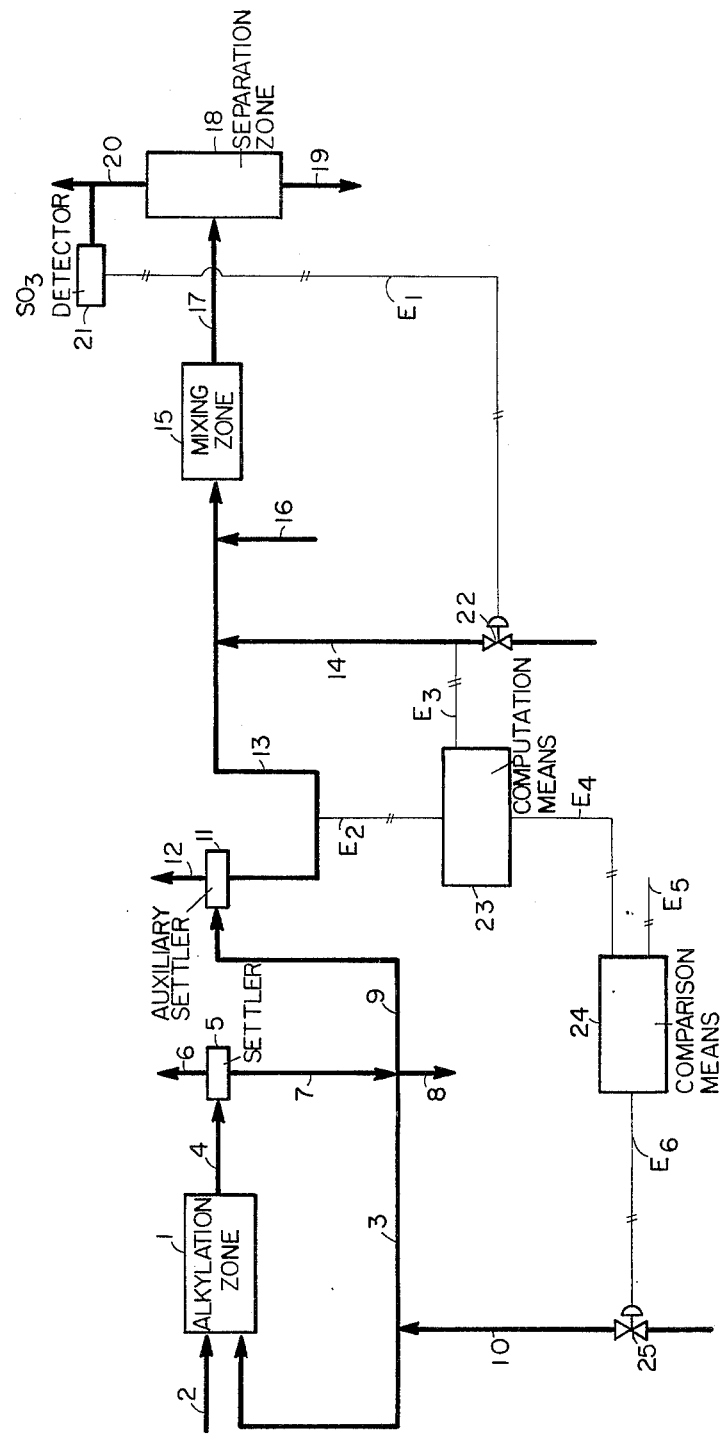

METHOD FOR CONTINUOUSLY CONTROLLING THE WATER CONTENT OF SULFURIC ACID ALKYLATION CATALYST

BACKGROUND OF THE INVENTION

1. Field of the Invention

This invention relates to a method for controlling the water content of a catalyst stream comprising water and a strong acid. More specifically, this invention concerns a method for continuously monitoring the water content of an alkylation catalyst comprising water and an acid selected from the group consisting of sulfuric acid and fluorosulfuric acid by adding fuming sulfuric acid to a sample of said catalyst at a rate sufficient to maintain the mixture thus formed at the point of incipient fuming and detecting the presence of the $SO_3$ evolved therefrom. The water content of the catalyst sample can then be determined from the flow rate of the sample and the flow rate and composition of the fuming sulfuric acid. The water content of the catalyst stream being monitored can then be controlled by regulating the addition rate of fresh acid to the alkylation process in accordance with the deviation between the actual water content and the desired water content.

2. Description of the Prior Art

The alkylation of isoparaffins with olefins in the presence of an acid catalyst such as sulfuric acid, fluorosulfuric acid and the like is well know in the petroleum refining art. Alkylation processes employing sulfuric acid have been extensively described in a number of publications (see, for example, "Petroleum Management", Vol. 33 (No. 13) pp. 203–215, Dec. 1961 and Vol. 34 (No. 1) pp. 207–217, Jan. 1962; "Petroleum Refiner", Vol. 37 (No. 9), pp. 316–329, Sept. 1958), the disclosures of which are incorporated herein by reference. Typically, in this process, an isoparaffin such as isobutane and olefins such as butenes are alkylated in the presence of a concentrated sulfuric acid catalyst which may range upward in strength from about 85 wt. % sulfuric acid. As the alkylation reaction proceeds, the strength of the acid catalyst, i.e. the activity, tends to decrease. This is due predominantly to dilution with water as well as to the formation of catalyst-hydrocarbon complexes. If the water content increases to too high a level, undesirable heavy alkylate will be produced. When the water content of the catalyst becomes very high, e.g., above about 5–6 wt. %, fresh acid makeup cannot be added to the system at a rate sufficient to maintain an acid strength conducive to stable operation. Furthermore, at such high water contents, the alkylation reaction ceases. We believe that these effects are due to the olefinic portion of the feed combining with the free sulfuric acid, i.e. the uncombined sulfuric acid, present in the catalyst to form dialkyl sulfates which preferentially accumulate within the hydrocarbon phase (due to their significantly higher solubility in the hydrocarbon relative to that in the acid) and thus deplete the acid catalyst inventory. If allowed to continue, substantially all of the catalyst inventory will be depleted. The acid (catalyst) phase remaining in the reaction zone will be predominantly monoalkylsulfates, water, carbonaceous complexes along with small amounts of dialkyl sulfates and sulfuric acid. This is not an alkylation catalyst. Therefore, it is desirable to maintain the acid strength above a certain minimum concentration relative to the water present in the catalyst to obtain a satisfactory operation. Should the acid strength drop below the established minimum, the catalyst inventory must be withdrawn from the reaction zone and replaced with fresh acid makeup.

In commercial operations, one method for determining and eventually controlling the free acid strength is by periodically measuring the titratable acidity of the acid stream, be it a fresh, intermediate or a spent acid stream. However, any monoalkyl sulfates present therein will titrate as equivalent to 0.5 of sulfuric acid so as to mask the trueamount of water present therein. Therefore, the measured free sulfuric acid strength will appear to be higher than the actual free sulfuric acid strength. Thus, the actual water/sulfuric acid ratio will be greater than indicated by this measurement. Another method for determining the free acid strength is to measure the amount of carbon and water in the acid stream since the wt. % free sulfuric acid will be equal to about 100 − wt. % carbon − wt. % water. Such measurements are normally done by one or more methods that are well known by one skilled in the alkylation art. However, either of the above methods for determining acid strength of the catalyst is time consuming and expensive when carried out in the laboratory and cannot be accomplished with sufficient rapidity for close operational control of the process.

When fluorosulfuric acid is employed as the alkylation acid, such as is described in U.S. Pat. No. 3,887,635, the disclosures of which are incorporated herein by reference, it is preferred to have essentially no free water present, although some may be present. However, the analytical techniques mentioned above may be used to determine the equivalent water present (i.e. the water equivalent to adding water, other oxygenated compounds or mixtures thereof to fluorosulfuric acid), but suffer from the deficiencies noted above.

It has also been suggested that the water content of a sulfuric acid catalyst can be determined by mixing fuming sulfuric acid with the acid catalyst until fuming is initiated (see Albright, L. F. et al, "Alkylation of Isobutane with Butenes: Effect of Sulfuric Acid Compositions", Ind. Eng. chem. Process Des. Devlop. Vol. 11 (No. 3), p. 446–450, 1972). However, neither this method nor any of the above-mentioned methods have been used to control continuously the water content of the acid catalyst by continuously controlling the addition rate of fresh acid to the alkylation process.

SUMMARY OF THE INVENTION

Now according to the present invention, it has been found that the water content of an alkylation catalyst comprising water and an acid selected from the group consisting of sulfuric acid and fluorosulfuric acid can be controlled continuously by intimately contacting a sample of said acid catalyst with a stream of fuming sulfuric acid and sensing the presence of the $SO_3$ thus formed. A signal from an $SO_3$ detector is developed in accordance with the sensed conditions such that the addition rate of fuming sulfuric acid to the acid catalyst stream is maintained at the point of incipient fuming; i.e. the point at which $SO_3$ is first evolved from the catalyst-fuming sulfuric acid mixture. The water content of the acid catalyst stream can be determined from the chemistry of the reaction, the flow ratio of the two acid streams and the free $SO_3$ concentration of the fuming sulfuric acid stream, i.e. the $SO_3$ in the fuming sulfuric acid that is not chemically combined. A control signal is developed in accordance with the water content thus determined and a signal corresponding to the desired water content. The control signal is then applied to control means which regulate the addition rate of fresh acid to the alkylation process so as to control the water content of the acid catalyst employed in said process. The acid catalyst stream referred to herein may be a catalyst stream employed at any point in the alkylation process; e,g, fresh, intermediate or spent acid catalyst.

BRIEF DESCRIPTION OF THE DRAWING

The single FIGURE is a block diagram illustrating the control system of the present invention applied to a typical alkylation process.

DESCRIPTION OF THE PREFERRED EMBODIMENT

Having thus described the invention in general terms, reference is now made to the FIGURE which shows one embodiment of the present invention for a spent sulfuric acid alkylation catalyst. Such details are included as are necessary for a clear understanding of how the present invention may be applied to controlling the water content of said acid catalyst. No intention is made to unduly limit the scope of the present invention to the particular configuration shown as variations obvious to those having ordinary skill in the art of controlling alkylation processes are included within the broad scope of the present invention.

Referring now to the FIGURE, there is shown a portion of an alkylation process in which an isoparaffin, e.g. $C_4$–$C_5$ (or higher) isoparaffin, is reacted with olefins, e.g., a $C_3$–$C_5$ (or higher) olefin, in a reaction zone in the presence of a sulfuric acid catalyst to form a reaction product having a higher molecular weight than that of the isoparaffin reactant or those products formed by self-alkylation. The reaction product is normally a mixture of $C_5$–$C_{14}$ saturates, often termed "alkylate", and typically contains a mixture of $C_7$–$C_9$ hydrocarbons, the specific composition of which depends upon the particular isoparaffin and olefinic reactants and the operating conditions utilized. Preferably, the olefin is propylene, butylene, amylene, $C_7$–$C_{14}$ polymers, or mixtures thereof and the isoparaffin, is isobutane.

As shown in the FIGURE, the isoparaffin and olefins enter alkylation reaction zone 1 via line 2 and contact a recycle acid stream introduced via line 3. The hydrocarbon-spent acid (spent catalyst) mixture formed in alkylation zone 1, often referred to as an "emulsion mixture", is then passed via line 4 to emulsion settler 5 wherein said mixture is separated from the spent acid. The hydrocarbon product is then discharged from settler 5 via line 6 and passed to additional separation facilities (not shown), e.g., fractionation zone, for recovery of the alkylate. The spent acid catalyst is removed from settler 5 via line 7 and a major portion thereof is recycled to alkylation zone 1 via line 3. A small portion of the acid catalyst not recycled to the alkylation zone is purged from the system via line 8. Typically, the acid catalyst purged has a titratable acidity in the range of 88–93% the preferred value varying with the molecular weight of the olefin. In general, this preferred strength decreases as the molecular weight of the olefin increases. A sample of the acid catalyst is shown leaving settler 5 via line 9. As an example of the relative magnitudes of streams 3, 7, 8 and 9, if 25,000 B/D of acid catalyst is discharged from settler 5 via line 7, typically from about 100 to about 300 B/D of acid catalyst would be withdrawn via line 8 while less than 50, preferably less than 20, more preferably less than 10 and typically from about 1–5 B/D would be removed via line 9. The remaining acid catalyst would be recycled to reaction zone 1 via line 3. fresh sulfuric acid makeup is added to recycle acid stream 3 via line 10 to maintain the desired catalyst inventory and acid strength in alkylation zone 1. Typically, the fresh sulfuric acid makeup has a titratable acidity of from 96–100%, preferably from 98–100%, on a hydrocarbon-complex-free basis. Consequently, 96% sulfuric acid means fresh sulfuric acid having 4% water. However, depending on the source, there may be some carbonaceous material present in the fresh sulfuric acid makeup. The fresh sulfuric acid makeup may be added to the system as shown in the FIGURE or at any convenient location in the recycle loop following emulsion settler 5 or, if desired, directly to well-mixed reaction zone 1.

The spent acid catalyst from settler 5 may contain small amounts of hydrocarbons that were not mechanically separated in settler 5. Such hydrocarbons will affect the specific gravity of the spent sulfuric acid catalyst stream in line 9 which can cause erroneous flow meter readings and hence false readings regarding the amount of water present in said stream. Therefore, the spent acid catalyst present in line 9 is passed to an auxiliary emulsion settler 11 to effect the substantial removal of entrained hydrocarbons from the catalyst. The hydrocarbons thus removed leave settler 11 via line 12 and a substantially hydrocarbon-free spent acid is discharged, preferably at a constant flow rate, via line 13. By substantially hydrocarbon-free is meant that the acid catalyst contains less than 1%, preferably less than 0.1%, mechanically separable hydrocarbons based on acid catalyst. The auxiliary emulsion settler 11 is operated at substantially the same temperature as emulsion settler 5.

The substantially hydrocarbon-free spent acid catalyst sample is then contacted with fuming sulfuric acid which is introduced into the system via line 14. Such fuming sulfuric acid is a readily available article of commerce. Preferably, the fuming sulfuric acid employed contains from about 102 to about 105 wt. % sulfuric acid. When the fuming sulfuric acid is contacted with the catalyst sample, water in the catalyst will react with the free $SO_3$ in the fuming sulfuric acid in accordance with the following equation:

$$H_2O + SO_3 \rightarrow H_2SO_4 \qquad (1)$$

Once substantially all of the water has been reacted according to equation (1), $SO_3$ will be evolved from the catalyst-fuming sulfuric acid mixture. Typically, the mixture fumes when it comprises from 100 to about 100.2 wt. % sulfuric acid.

The amount of fuming sulfuric acid added relative to the spent acid catalyst present in line 13 depends upon the flow rate of said acid catalyst and the amount of water present therein, as well as the concentration of free $SO_3$ in the fuming sulfuric acid added to the system. For example, if a 100 gm per unit time spent acid sample containing 90% free sulfuric acid, 4% water and 6% carbonaceous material is intimately contacted with a stream of fuming sulfuric acid containing 103.15 wt. % sulfuric acid (14 wt. % free $SO_3$), the amount of fuming sulfuric acid required to cause fuming according to equation (1), assuming the fuming starts at 100 wt. % acid) is 67 cc per unit time. Therefore, each 0.1 wt. % water in the spent acid requires the addition of about 1.67 cc (1.27 gms) per unit time of the 103.15 wt. % fuming sulfuric acid to produce fuming of the mixture. It should be pointed out that the stronger the fuming sulfuric acid, the less that need be added. However, more accurate control is possible by use of weaker fuming acid.

The spent acid catalyst-fuming sulfuric acid mixture is then passed into a mixing zone 15 to provide a substantially uniform mixture of the two acid streams to ensure that the $SO_3$ present in the fuming sulfuric acid will have reacted with the water in the spent acid. The mixing can be accomplished in any convenient manner provided the acid streams are intimately mixed. Examples of suitable mixing means include a series of orifice mixers, mechanical stirrers, and the like. If orifice mixers are employed, it is preferred to have at least six in series with a total pressure drop of at least 15 psi.

It is desirable, although not necessary to the practice of the present invention, that an inert gas such as nitrogen be contacted with the spent acid catalyst-fuming sulfuric acid mixture prior to entering the mixing chamber 15 to facilitate release of sufficient gas phase to enable subsequent detection of $SO_3$. The gas can be any gas that is inert to the spent acid catalyst-fuming sulfuric acid mixture. The amount of inert gas added is not critical provided it is sufficient to facilitate the release of a major portion of the excess $SO_3$ from the acid mixture, i.e. a major portion of the excess free $SO_3$ equivalent to the wt. % $H_2SO_4$ above 100 is stripped from the acid mixture. For example, if the mixture is 100.1% $H_2SO_4$ and if the stripped acid mixture will contain about 100.02 wt. % $H_2SO_4$ (based on carbonaceous complex-free catalyst), about 80% of the $SO_3$ will be released from the mixture due to introduction of the inert gas. Preferably, the flow ratio of inert gas to the catalyst sample should be maintained substantially constant to obtain about the same relative degree of stripping.

The substantially uniform mixture is then passed via line 17 into separation zone 18 wherein said mixture is separated into a gas phase and an acid mixture phase. The acid mixture phase comprises sulfuric acid catalyst and is discharged from separation zone 18 via line 19. The gas phase comprises inert gas as well as any small quantities of volatile hydrocarbon not removed in auxiliary emulsion settler 5. Although it is desirable that the acid catalyst-fuming sulfuric acid mixture be maintained at the point of incipient fuming, it is possible that $SO_3$ may not be present in the vapor stream since more water may be present relative to the $SO_3$ being added such that substantially all of the free $SO_3$ is reacted with the water. Small amounts of dissolved $SO_3$ may also be present in the acid mixture phase. The separation zone may be any suitable apparatus for separating vapor and liquid mixtures. Internal packing and trays are not required provided the separation zone is designed to comprise sufficient cross-sectional area and disengaging height above the liquid level to prevent the presence of entrained liquid in the gas phase.

The gas phase is then discharged from separation zone 18 via line 20 and a portion thereof introduced into $SO_3$ detector 21 which senses the presence of $SO_3$ therein. The detector can be any suitable apparatus for sensing $SO_3$ continuously. One example of such an apparatus is described in Oil and Gas Journal, Vol. 66, p. 89, Apr. 15, 1968, the disclosures of which are incorporated herein by reference. A control signal E1 from the $SO_3$ detector is developed in accordance with the sensed conditions such that the addition rate of fuming sulfuric acid via line 14 to the acid catalyst sample in line 13 is maintained at the point of incipient fuming, i.e. the point where $SO_3$ is first evolved from the spent acid catalyst-fuming sulfuric acid mixture above a threshold level present due to the partial pressure of $SO_3$ at the operating conditions. Typically, this threshold level is less than 0.1 mm of mercury for both sulfuric acid and fluorosulfuric acid systems. The control signal E1 is then transmitted to control means 22 which regulates the flow rate of fuming sulfuric acid such that the presence of $SO_3$ in the gas phase 20 is maintained at substantially incipient conditions. A control signal E2 corresponding to the flow rate of the acid catalyst sample and a control signal E3 corresponding to the flow rate and the free $SO_3$ concentration of fuming sulfuric stream 14 are then introduced into computation means 23 which calculates by material balance, according to the chemistry of the reaction shown in equation (1), the amount of water present in the stream 13. Suitable computation means can be selected from a variety of digital or analog computing devices, depending upon the particular application. For example, the computation means could be a large computer capable of controlling an entire refinery complex or, if desired, a minicomputer designed for more limited applications. Such computations are well known articles of commerce and thus are readily available in the marketplace.

The water content thus calculated is then developed into a control signal E4 and sent to a comparison means 24 which compares signal E4 with a signal E5 corresponding to the desired water content of the acid catalyst stream being monitored such that a control signal E6 is generated. The control signal E6 is then applied to control means 25 which regulates the addition rate of fresh acid of known water content to maintain the desired water content in the acid catalyst stream being monitored.

Thus, according to the present invention, when the water present in the sulfuric acid catalyst sample contacts the fuming sulfuric acid containing free $SO_3$, the water and free $SO_3$ react according to equation (1) above until substantially all of the water is reacted. The presence of $SO_3$ above the threshold value is then sensed by the $SO_3$ detector causing the addition rate of the fuming sulfuric acid to be varied such that the acid catalyst-fuming sulfuric acid mixture will be maintained at the point of incipient fuming. The water content of the catalyst sample can then be determined by material balance from the chemistry of the reaction (equation (1)) knowing the flow rate of the sample, and the flow rate and free $SO_3$ concentration of the fuming sulfuric acid. Thus, the control system described herein seeks the maintain the acid mixture at the point of incipient fuming to enable determination of the water content of the acid catalyst. The calculated (actual) water content of the sample of the catalyst stream being monitored is then compared with the desired water content, and the addition rate of fresh acid of known water content is controlled such that the desired water content will be obtained in a selected period of time. A change in the water content of the catalyst sample will cause a change in the $SO_3$ sensed which will in turn effect a change in the addition rate of the fuming sulfuric acid such that a new water content will be calculated. As before, the newly calculated water content will then be compared with the desired value such that the addition rate of fresh acid will be adjusted to match the desired water content in the selected period of time.

In an analogous manner, when the alkylation catalyst comprises fluorosulfuric acid, the present invention may be used to determine the equivalent water present in the particular acid catalyst stream being monitored (i.e. the water equivalent to adding water, other oxygenated compounds or mixtures thereof to fluorosulfuric acid) by sensing the presence of $SO_3$ as described above and according to the chemistry of the following reactions:

$$HF + SO_3 \rightarrow HSO_3F \quad (2)$$

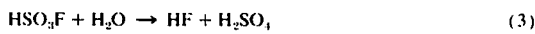
$$HSO_3F + H_2O \rightarrow HF + H_2SO_4 \quad (3)$$

The water content of the acid catalyst stream being monitored (the acid ctalyst sample) is then compared with the desired water content of said stream such that the addition rate of fresh acid is regulated to maintain the desired water content of said stream.

In general, the water content of the acid catalyst can vary depending upon, for example, the molecular weight of the olefin, the temperature, the olefin space velocity. However, factors that will compensate for losses in catalyst activity as the water content increases, e.g. increased temperature, decreased olefin space velocity and the like, would be expected to permit operations at higher water contents. The amount of water in the acid stream being monitored may range broadly and is normally determined by the economics of the specific operations. Generally, for a sulfuric acid catalyst, the water content of said catalyst should be maintained between about 0.3 and about 4 wt. %, preferably between about 0.5 and about 3.5 wt. %, and more preferably between 1 and about 2.5 wt. %, based on acid catalyst. However, for a fluorosulfuric acid catalyst, the water content of said catalyst should be maintained between about 1 and 18 wt. %, preferably between about 3 and about 10 wt. %, based on acid catalyst. As the alkylation temperature is increased, higher water contents are permissible. By using the present invention, the water content of the acid stream can be maintained within plus or minus 1%, preferably within plus or minus 0.5 wt. %, and more preferably within plus or minus 0.2 wt. %, based on acid catalyst, of the desired value.

The temperature of the present invention may also range broadly but should be maintained at a level sufficient to avoid freezing of an acid stream at any point in the system. Thus, the temperature should be maintained above the melting point of the acid stream at any point in the system, be it fuming sulfuric acid stream, the acid stream being monitored (either sulfuric acid or fluorosulfuric acid), or a mixure of the two. In general, the present invention should be operated at a pressure sufficiently low to avoid the evolution, at the particular temperature of the system, of light hydrocarbons, e.g. isobutane, from the acid stream being monitored.

Control means (e.g. valve means), sensing means (e.g. flow orifices), comparison means (e.g. conventional digital or analog controllers), the means for obtaining the catalyst sample (e.g. a probe), and the like equipment are well known articles of commerce and, as such, are readily available from various vendors.

What is claimed is:

1. In an alkylation process wherein an isoparaffin is reacted with olefins in the presence of an acid catalyst to provide an acid catalyst-hydrocarbon mixture to a settling zone wherein a hydrocarbon product is separated from the acid catalyst, a major portion of the acid catalyst from said settling zone is being recycled to the alkylation zone, and wherein fresh acid is being added to said alkylation process, the improvement which comprises continuously controlling the water content of the acid catalyst by continuously controlling the addition rate of fresh acid to said alkylation process, said catalyst comprising sulfuric acid including water according to the steps of:
    1. withdrawing a sample of the acid catalyst from said settling zone,
    2. intimately contacting said sample with a stream of fuming sulfuric acid in an amount sufficient to ensure substantially complete reaction of the water present in said sample with the $SO_3$ present in said fuming sulfuric acid and thereby forming concentrated acid having substantially no free water present therein;
    3. sensing the presence of $SO_3$ evolved in step (2) after said complete reaction of the water present in said sample said sensed presence of $SO_3$;
    4. controlling the rate of fuming sulfuric acid addition in step (2) in response to the control signal of step (3) such that said concentrated acid in step (2) is at the point of incipient fuming;
    5. sensing the flow rate of the sample being withdrawn in step (1) and the flow rate of said fuming sulfuric acid stream being added in step (2);
    6. providing a signal corresponding to the water content of the sample of step (1) in accordance with the sensed flow rate of said sample and the flow rate of said fuming sulfuric acid of step (5);
    7. providing a reference signal in a computation means corresponding to a desired water content in said acid catalyst;
    8. comparing the signals from steps (6) and (7) to provide a control signal;
    9. controlling the addition rate of fresh acid catalyst to said process in accordance with the control signal from step (8) and thereby controlling the water content of the acid catalyst during the alkylation process.

2. The process of claim 1 wherein said acid is sulfuric acid and the water content of the acid catalyst ranges from about 0.3 to 4 wt. %, based on acid catalyst.

3. The process of claim 2 wherein the water content of the acid catalyst is maintained within plus or minus 0.5 wt. %, based on acid catalyst, of said desired water content.

4. The process of claim 1 wherein the contacting of step (2) is effected in the presence of an inert gas.

5. The process of claim 4 wherein the inert gas is nitrogen.

6. The process of claim 1 wherein the concentrated acid from step (2) is separated into a gas phase comprising $SO_3$ and a liquid phase comprising said acid.

7. The process of claim 1 wherein the acid catalyst of step (1) contains less than 1 wt. % mechanically separable hydrocarbons based on acid catalyst.

* * * * *

UNITED STATES PATENT OFFICE
CERTIFICATE OF CORRECTION

PATENT NO. : 4,018,846
DATED : April 19, 1977
INVENTOR(S) : Ivan Mayer

It is certified that error appears in the above-identified patent and that said Letters Patent are hereby corrected as shown below:

At column 5, line 3, delete "1.27" and insert in place thereof --3.17--.

At column 8, line 28, after "said sample" insert --and providing a control signal in accordance with--.

Signed and Sealed this

Twenty-fifth Day of October 1977

[SEAL]

Attest:

RUTH C. MASON
Attesting Officer

LUTRELLE F. PARKER
Acting Commissioner of Patents and Trademarks